US006627229B2

(12) United States Patent
Kikuchi et al.

(10) Patent No.: US 6,627,229 B2
(45) Date of Patent: Sep. 30, 2003

(54) ANTIVIRAL AGENT AND METHOD OF PRODUCING THE SAME

(75) Inventors: Kazutomo Kikuchi, Sendai (JP); Noriaki Kikuchi, Sendai (JP)

(73) Assignee: Hiromi Houzawa, Iwata-ken (JP)

( * ) Notice: Subject to any disclaimer, the term of this patent is extended or adjusted under 35 U.S.C. 154(b) by 0 days.

(21) Appl. No.: 09/888,267

(22) Filed: Jun. 23, 2001

(65) Prior Publication Data

US 2001/0043953 A1 Nov. 22, 2001

(51) Int. Cl.[7] ........................ A61K 35/56; A61K 35/32; A61K 33/06; A61K 33/10; A01N 63/02

(52) U.S. Cl. ....................... 424/547; 424/405; 424/489; 424/520; 424/538; 424/548; 424/549; 424/572; 424/581; 424/675; 424/678; 424/682; 424/686; 424/687; 424/688; 424/693; 424/694; 424/695; 424/696; 424/715; 424/722; 514/849; 514/888; 514/898; 514/934; 514/951

(58) Field of Search ................................ 424/520, 538, 424/547–549, 572, 581, 675, 678, 682, 686–688, 693–696, 715, 722, 405, 489; 514/849, 888, 898, 934, 951

(56) References Cited

U.S. PATENT DOCUMENTS

| | | | | | |
|---|---|---|---|---|---|
| 1,001,375 A | * | 8/1911 | Edwards | ..................... | 426/473 |
| 5,084,279 A | * | 1/1992 | Kato et al. | .................. | 424/547 |
| 5,296,246 A | | 3/1994 | Inoue et al. | .................. | 426/74 |
| 5,409,714 A | * | 4/1995 | Ishijima | ...................... | 424/693 |
| 6,365,193 B1 | * | 4/2002 | Sasaki et al. | ............... | 424/538 |
| 2001/0043953 A1 | * | 11/2001 | Kikuchi et al. | ............. | 424/687 |

FOREIGN PATENT DOCUMENTS

| | | | |
|---|---|---|---|
| CA | 2201025 | | 9/1998 |
| EP | 0 393 267 | | 10/1990 |
| JP | 3-21342 | | 1/1991 |
| JP | 7-170939 | | 7/1995 |
| JP | 7-194338 | | 8/1995 |
| JP | 8-53358 | | 2/1996 |
| JP | 9-323935 | | 12/1997 |
| JP | 11-199403 | | 7/1999 |
| JP | 11-266796 | | 10/1999 |
| JP | 2001226210 | * | 8/2001 |
| WO | WO 93/11670 | | 6/1993 |
| WO | 94/09798 | * | 5/1994 |
| WO | WO 00/38526 | | 7/2000 |
| WO | 200072685 | * | 12/2000 |

OTHER PUBLICATIONS

Chemical Abstracts 133: 70193, abstracting JP 2000191417 (Jul. 2000).*

Chemical Abstracts 114:95160, abstracting JP 02/273621 (Nov. 1990).*

Chemical Abstracts 120:200109, abstracting JP 05/169069 (Jul. 1993).*

Chemical Abstracts 112:25670, abstracting JP 01/117833 (May 1989).*

Derwent Abstract, accession No. 1991–143135, abstracting JP 03/077802 (Apr. 1991).*

JAPIO Abstract, accession No. 1982–125676, abstracting JP 57–125676 (Aug. 1982).*

JAPIO Abstract, accession No. 1982–144949, abstracting JP 57–144949 (Sep. 1982).*

Derwent Abstract, accession No. 1993–357138, abstracting JP 05–262655 (Oct. 1993).*

Chemical Abstracts 102:23196, abstracting JP 59–156914 (Sep. 1984).*

Chemical Abstracts 101:177501, abstracting JP 59–111918 (Jun. 1984).*

JAPIO Abstract, accession No. 1995–124462, abstracting JP 07–124462 (May 1995).*

U.S. patent application Ser. No. 09/869,068 (Jun. 22, 2001).

European Search Report, from EPO Communication dated Dec. 7, 2001, is attached.

* cited by examiner

*Primary Examiner*—John Pak
(74) *Attorney, Agent, or Firm*—Paul A. Guss

(57) ABSTRACT

An antiviral agent of an antiviral ability against various viruses and a method of producing the same are provided. A heat treatment is applied to a calcium-containing substance represented by calcium carbonate-containing substances originating from the animal such as clamshell, eggshell, crustacean shell, bone, coral, and pearl, and calcium carbonate-containing minerals such as limestone. When a temperature of the heat treatment is not less than 650° C. and less than a melting point of the calcium component-containing substance, a sufficient time of the heat treatment is 2 to 13 hours.

7 Claims, 2 Drawing Sheets

FIG. 2

| TEST NO. | $TCID_{50}$ AT EACH REACTION TIME [$ml^{-1}$] | | | | |
|---|---|---|---|---|---|
| | 0 MINUTE | 5 MINUTES | 15 MINUTES | 30 MINUTES | 60 MINUTES |
| EXAMPLE 1 | $6.0\times10^{7}$ | $4.0\times10^{3}$ | $4.0\times10^{3}$ | $4.0\times10^{3}$ | $2.0\times10^{3}$ |
| COMPARATIVE EXAMPLE 1 | $6.0\times10^{7}$ | — | — | — | $2.0\times10^{7}$ |
| EXAMPLE 2 | $4.0\times10^{6}$ | $<1.2\times10^{3}$ | $<1.2\times10^{3}$ | $<1.2\times10^{3}$ | $<1.2\times10^{3}$ |
| COMPARATIVE EXAMPLE 2 | $4.0\times10^{6}$ | — | — | — | $2.6\times10^{6}$ |
| EXAMPLE 3 | $4.0\times10^{7}$ | $<1.2\times10^{4}$ | $<1.2\times10^{4}$ | $<1.2\times10^{4}$ | $<1.2\times10^{4}$ |
| COMPARATIVE EXAMPLE 3 | $4.0\times10^{7}$ | — | — | — | $8.0\times10^{6}$ |
| EXAMPLE 4 | $1.2\times10^{5}$ | $<1.2\times10^{3}$ | $<1.2\times10^{3}$ | $<1.2\times10^{3}$ | $<1.2\times10^{3}$ |
| COMPARATIVE EXAMPLE 4 | $1.2\times10^{5}$ | — | — | — | $1.2\times10^{5}$ |

ANTIVIRAL AGENT AND METHOD OF PRODUCING THE SAME

BACKGROUND OF THE INVENTION

1. Field of the Invention

The present invention relates to an antiviral agent and a method of producing the same. In particular, the present invention relates to an antiviral agent of an excellent antiviral ability against various viruses without releasing any substance to damage health of animals and plants. The present invention also relates to a method of producing the same.

2. Description of the Related Art

As a sterilizing treatment, fish and shellfish are immersed in an aqueous solution containing sodium hypochlorite before being shipped to fish shops, department stores, supermarkets or the like. The fish is transported after being frozen. Further, the so-called shucked raw shellfish of scallop and oyster to be eaten is transported after it is accommodated in a container and is maintained at a temperature of 5 to 6° C.

The sterilizing treatment and the transport at the low temperature prevent food poisoning by decreasing the number of bacteria. That is, the sterilizing treatment greatly reduces the number of bacteria including pathogenic *Escherichia coli* such as O-157, cell-invasive bacteria, Salmonella or the like. Further, a minute amount of the surviving bacteria does not propagate at the low temperature. Therefore, the number of bacteria can be kept small until the fish and the shellfish are eaten. In other words, since the number of bacteria such as O-157 and Salmonella does not increase at the low temperature, probability of the bacterial food poisoning is greatly low in winter.

However, it is often reported that one presents a symptom of the food poisoning although he or she eats in winter the sterilized seafood which has been transported at the low temperature. Recent studies elucidate that the above food poisoning is not a bacterial one but is a viral one which is caused by the virus including spherical small virus (hereinafter referred to as "SRSV"), astrovirus, rotavirus or the like.

In the viral food poisoning, the above viruses parasitic on the seafood invade a human body if he or she eats the seafood that is not heat-treated. Next, the viruses propagate while destroying mucosal cells of bowels or the like and, as a result, induce enterogastritis symptoms such as diarrhea, emesis, fever or the like. Actually, if the bacteria is not detected in the vomit and excreta of a person who presents the symptom of the food poisoning, the viruses are detected in many cases. Since SRSV is detected frequently in particular, it is supposed that almost all of the viral food poisoning may be caused by SRSV.

For preventing the viral food poisoning, it is assumed to use a substance which reduces the number of viruses and which inhibits the viral propagation for a long period of time. However, a method of cultivating SRSV has not been established yet and it is greatly difficult to investigate what kind of substance is able to be antiviral against SRSV. At present, sodium hypochlorite is used as a usual sterilant on the assumption that it may be effective to SRSV as well. However, as described above, the viral food poisoning is generated in some cases even if the seafood immersed in the aqueous sodium hypochlorite solution is eaten and even the sodium hypochlorite cannot completely prevent the viral food poisoning.

Further, liberated from sodium hypochlorite, chlorine sometimes adheres to the seafood that is sterilized with the aqueous sodium hypochlorite solution. The chlorine is well known as a toxic substance, and the mucous membrane of lungs, nostril or the like is damaged if the chlorine is ingested at a high concentration. Furthermore, there is a possibility that arteriosclerosis occurs due to constant and continuous ingestion of the chlorine whose concentration is even low. That is, it is not favorable for the health to eat the seafood adhered with the liberated chlorine.

Further, if the liberated chlorine is reacted with an organic matter remaining in tap water as a solvent, carcinogenic methane trihalide (trihalomethane) is generated and adheres to the seafood. It is not favorable for the health to eat the seafood adhered with the carcinogenic substance.

As understood from the above, there is a problem that it is not favorable for the human health to sterilize the seafood with the aqueous sodium hypochlorite solution.

SUMMARY OF THE INVENTION

It is an object of the present invention to provide an antiviral agent of an antiviral ability against various viruses and of a possible antiviral ability against SRSV as well without releasing any substance to damage health of animals and plants, and a method of producing the same. The "antiviral ability" in the present invention is a term to indicate abilities to kill the virus and to prevent the virus from propagating.

Even a substance of an antiviral ability against a certain virus is not always able to be antiviral against SRSV. Therefore, it is necessary to determine whether or not the substance has the antiviral ability against SRSV by contacting the substance and SRSV with each other to perform a cultivation test.

However, a nature of SRSV has not been clarified yet. Although a method of detecting SRSV is established, methods of cultivating SRSV and of confirming life or death thereof have not been established. For this reason, it is greatly difficult to develop an agent of the antiviral ability against SRSV, i.e., the ability to greatly decrease the number of viruses of SRSV for a short period of time. That is, it is impossible to confirm efficacy of the medicine because it is impossible to confirm the life or the death of SRSV. Accordingly, National Institute of Health is of the opinion that a substance possibly has the antiviral ability against SRSV virus as well if it has the antiviral ability against herpes simplex virus type 1, adenovirus type 3, influenza virus type A, and coxsackie virus group B type 1 which are representative viruses in classification.

That is, as well known, the virus is roughly classified depending on whether the nucleic acid coated with capsid is deoxyribonucleic acid (DNA) or ribonucleic acid (RNA). The virus is finely classified depending on whether or not it possesses envelope for coating capsid. The nucleic acid of herpes simplex virus type 1 and adenovirus type 3 is DNA, wherein the former has the envelope, and the latter does not have the envelope. By contrast, the nucleic acid of influenza virus type A and coxsackie virus group B type 1 is RNA, wherein the former has the envelope, and the latter does not have the envelope. National Institute of Health is the opinion that a substance of the antiviral ability against all the viruses of these types is highly possibly one of the antiviral ability against almost all the viruses including SRSV.

Taking these opinions into consideration, the present inventors have repeatedly investigated a substance of the antiviral ability against the above respective viruses, and thus the present invention has been consequently completed.

That is, the present invention resides in an antiviral agent comprising an active ingredient of a heat-treated calcium component-containing substance.

The calcium-containing substance expresses the antiviral ability if it is heat-treated.

Since the antiviral agent does not release any substance to damage health of animals and plants, fish and shellfish are neither dead nor sickened even if they are put in water containing the antiviral agent. In addition, since the fish and the shellfish take the water at the same time when they breathe, a dissolved ingredient of the antiviral agent in the water is also taken and kills the viruses in the fish and the shellfish. Thus, the antiviral agent of the present invention kills only the viruses easily and simply without killing and sickening the fish and the shellfish. Similarly, the antiviral agent can kill the viruses adhering to vegetables. The health of humans and animals is not damaged even if they take the animals and the plants whose viruses are sterilized by the antiviral agent.

Furthermore, the antiviral agent can prevent the bacterial food poisoning by killing the Salmonella, the *Escherichia coli* or the like as well as the viral food poisoning.

The calcium component-containing substance is preferably exemplified by at least one of a calcium carbonate-containing substance originating from an animal and a calcium carbonate-containing mineral. More specifically, it is possible to exemplify limestone and at least one selected from a group consisting of clamshell, eggshell, crustacean shell, bone, coral, and pearl.

The calcium carbonate-containing substance originating from the animal is originally waste. The calcium carbonate-containing mineral such as limestone is a natural product. Therefore, it is possible to furnish the raw material and is possible to provide the antiviral agent inexpensively.

Especially, when oyster shell is used as the clamshell, it is possible to obtain the fast-acting antiviral agent of an excellent antiviral activity. Therefore, it is preferable to use the oyster shell.

The preferable antiviral agent is powder having an average particle size of not more than 10 $\mu$m. Such an average particle size increases the contact area of the antiviral agent with the virus, thereby further improving the antiviral ability.

The heat-treated calcium-containing substance has the antiviral ability against herpes simplex virus type 1, adenovirus type 3, influenza virus type A, coxsackie virus group B type 1 or the like which are representative viruses in classification, thereby decreasing the number of these viruses.

In another aspect, the present invention resides in a method of producing an antiviral agent, comprising a heat treatment step of heat-treating a calcium component-containing substance.

Accordingly, the calcium component-containing substance expresses the antiviral ability.

The calcium component-containing substance is preferably heat-treated such that the temperature is not less than 650° C. and less than a melting point thereof. In this case, the sufficient heat treatment time is 2 to 13 hours.

The method preferably comprises, after the heat treatment step, a pulverizing step of pulverizing the heat-treated calcium component-containing substance so that an average particle size can be not more than 10 $\mu$m since the contact area of the pulverized calcium-containing substance with the virus is increased. Therefore, it is possible to obtain the antiviral agent of the excellent antiviral ability.

The method preferably comprises, before the heat treatment step, a pre-pulverizing step of pulverizing the calcium component-containing substance so that an average particle size can be 100 $\mu$m to 20 mm. By pre-pulverizing the calcium component-containing substance into a granular form, the heat treatment is enhanced in the heat treatment step in a short period of time uniformly from the surface to the inside of the granular calcium component-containing substance.

At least one of a calcium carbonate-containing substance originating from an animal and a calcium carbonate-containing mineral is preferably used as the calcium component-containing substance. More specifically, at least one selected from the group consisting of clamshell, eggshell, crustacean shell, bone, coral, and pearl is preferably used as the calcium carbonate-containing substance originating from the animal, and limestone is preferably used as the calcium carbonate-containing mineral. As described above, the calcium carbonate-containing substance originating from the animal is originally the waste. By contrast, the calcium carbonate-containing mineral such as limestone is the natural product. Therefore, it is possible to supply the raw material for the antiviral agent inexpensively.

Before the heat treatment step, it is preferable to provide a washing step of washing the calcium carbonate component-containing substance originating from the animal which is used as the calcium component-containing substance. Accordingly, it is possible to prevent malodor in the heat treatment step and damage of a heat treatment apparatus from being generated.

When clamshell, which has been left to stand for the elapse of time of not less than two years after removing a living body of clam therefrom, is used as the calcium carbonate-containing substance originating from the animal, the malodor is not generated and the heat treatment apparatus is not damaged, even if the heat treatment step is performed without the washing treatment. In other words, the washing treatment is not necessary. Therefore, the production efficiency of the antiviral agent is improved.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 2 shows $TCID_{50}$ in Examples 1 to 4 and Comparative Examples 1 to 4.

DESCRIPTION OF THE PREFERRED EMBODIMENTS

Figure 1:
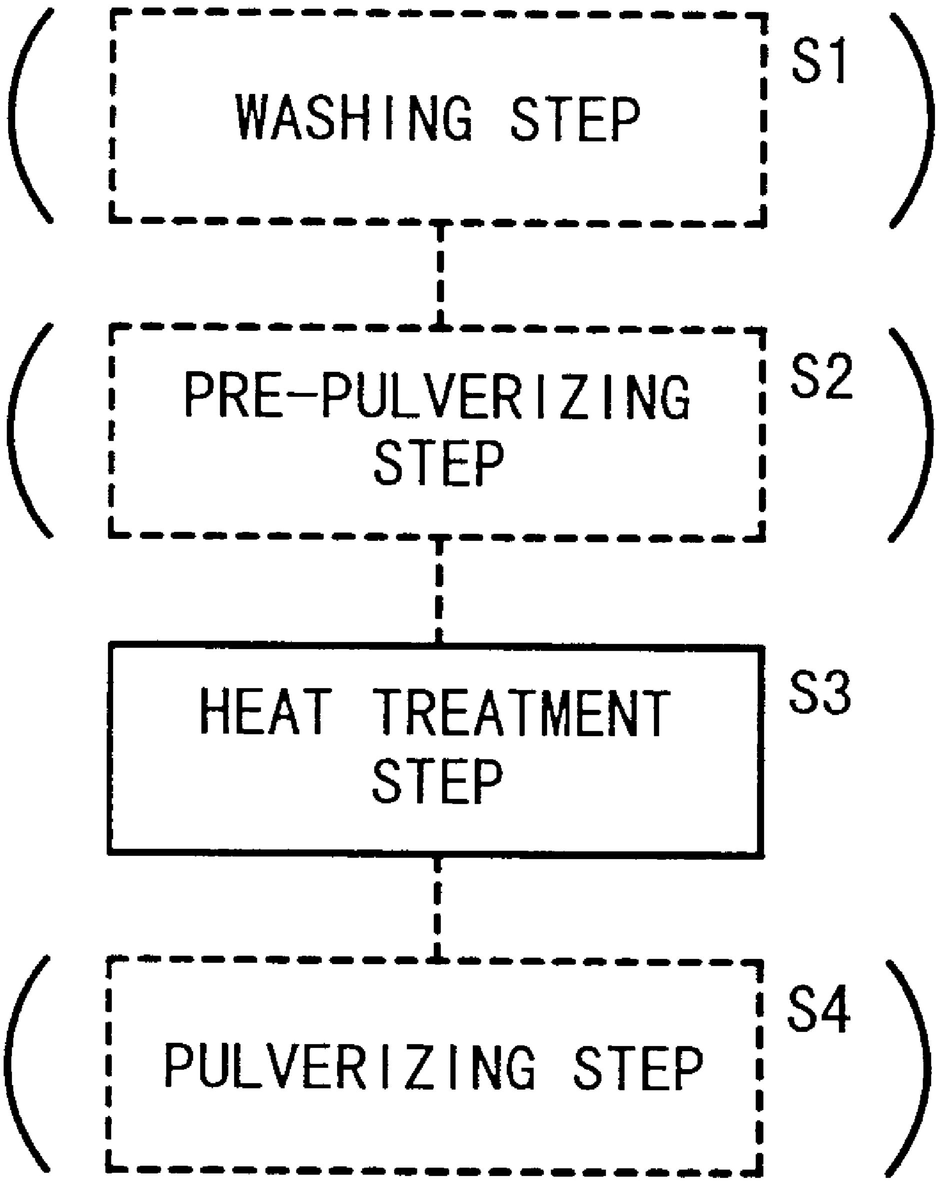
FIG. 1 shows a flow chart illustrating a method of producing an antiviral agent according to an embodiment of the present invention.

The antiviral agent and the method of producing the same according to the present invention will be explained in detail below with reference to the accompanying drawings, as exemplified by preferred embodiments.

The antiviral agent according to the embodiment of the present invention contains an active ingredient of a heat-treated calcium component-containing substance. The calcium component-containing substance refers to a substance containing calcium or a calcium compound such as calcium oxide, calcium phosphate, calcium carbonate, calcium lactate, and calcium hydroxide.

The calcium component-containing substance is not specifically limited provided that the substance contains calcium or the above calcium compound. It is possible to use commercially available calcium compound reagents such as calcium oxide reagent, calcium phosphate reagent, calcium carbonate reagent, calcium lactate reagent, and calcium hydroxide reagent, and a mixture of at least two reagents selected therefrom. However, it is more preferable to use at least one selected from a group consisting of calcium carbonate-containing substances originating from the animal, i.e., clamshell, eggshell of bird, duckbill or the like, shell of crustacean such as crab, bone of vertebrate, and coral. Since the above materials are originally treated as waste or exist naturally, they are available inexpensively and exist abundantly. Therefore, it is possible to produce the antiviral agent at low cost and, consequently, is possible to inexpensively supply a large amount of the antiviral agent. Further, it is also possible to decrease a burden to the environment because the amount of the wasted materials is reduced. Further, it is possible to obtain the virus-reducing agent of the virus-reducing ability which is more excellent than that using the above reagents as the raw materials.

It is also possible to use pearl as the calcium carbonate-containing substance although the pearl is not the waste. In this case, when the pearl of an inferior quality and unsuitable for accessories is used, it is possible to produce the antiviral agent at low cost.

Among the above calcium carbonate-containing substances originating from the animal, when clamshell, especially oyster shell is used as the raw material, it is possible to obtain the antiviral agent of an excellent antiviral ability.

Therefore, it is more preferable to use clamshell, especially oyster shell.

Another preferable example of the calcium component-containing substance is calcium carbonate-containing minerals, i.e., limestone or the like. Since the limestone is a natural product, it is also possible to produce the antiviral agent at low cost by using it.

The above calcium component-containing substance may be either one type of material or a mixture of two types of materials. For example, clamshell, coral, and calcium lactate reagent may be mixed which have been heat-treated respectively. Alternatively, a mixture of clamshell, coral, and calcium lactate reagent may be heat-treated.

The antiviral agent according to the embodiment of the present invention is able to decrease the number of the viruses of various types, and the ability of decreasing the number thereof continues for a long period of time. Therefore, the number of viruses is not increased as well. The antiviral agent according to the embodiment of the present invention is able to be antiviral against the viruses such as adenovirus type 3, herpes simplex virus type 1, coxsackie virus group B type 1, and influenza virus type A. These viruses are representative ones in classification.

The preferable antiviral agent is powder having an average particle size of not more than 10 $\mu$m. The antiviral ability is then further improved because a contact area of antiviral agent with the virus is increased.

A method of producing the above antiviral agent will now be explained with reference to FIG. 1 as a flow chart. The production method comprises a washing step S1 of washing the calcium component-containing substance, a pre-pulverizing step S2 of pulverizing the washed calcium component-containing substance into 100 $\mu$m to 20 mm, a heat treatment step S3 of heat-treating the calcium component-containing substance, and a pulverizing step S4 of pulverizing the heat-treated calcium component-containing substance into not more than 10 $\mu$m. The washing step S1, the pre-pulverizing step S2, and the pulverizing step S4 may be performed if necessary. Therefore, these steps are depicted with parentheses in FIG. 1.

When the above calcium carbonate-containing substance originating from the animal, i.e., at least one selected from the group consisting of clamshell, eggshell of bird, duckbill or the like, shell of crustacean such as crab, bone of vertebrate, coral, and pearl is used as the calcium-containing substance, pieces of meat, organic matters or bacteria or the like adhered thereto are removed at first in the washing step S1. Without the washing step S1, the malodor is generated in the heat treatment step S3. Originating from the pieces of meat, the organic matters or the like which are adhered to the calcium carbonate-containing substance originating from the animal, the residual matter remains in the antiviral agent in some cases. As a result, the antiviral ability of the antiviral agent is not excellent in some cases. Further, a heat-generating element or the like of a heat treatment apparatus may be damaged in a short period of time. Although the washing method is not specifically limited, it is exemplified by the washing with the high pressure jetted water or with the ultrasonic wave.

That is, the washing step S1 is preferably performed when the antiviral agent is produced by using the calcium carbonate-containing substance originating from the animal as the raw material. If any other calcium component-containing substance such as the above commercially available reagent or the like is used as the raw material, the washing step S1 is not necessary. In the latter case, the residual matter originating from the pieces of meat, the organic matters or the like does not remain in the antiviral agent. Furthermore, the heating element or the like of the heat treatment apparatus is not damaged in a short period of time.

It is also not necessary to perform the washing step S1 when clamshell is used which has been left to stand for the elapse of time of not less than two years after removing a living body of clam therefrom. The organic matters or the like adhered to the surface of the clamshell are subjected to efflorescence or deliquescence, thereby being spontaneously removed. Further, the adductor muscle or the like remaining upon removing the living body of clam has been decomposed and omitted therefrom. That is, when the above clamshell is used as the raw material, it is not necessary to perform the washing step S1, and the antiviral agent can be efficiently produced. Therefore, the above procedure is preferred. The malodor is not generated in the heat treatment step S3.

Subsequently, in the pre-pulverizing step S2, the calcium component-containing substance is pulverized to have an average particle size of 100 $\mu$m to 20 mm. When the calcium component-containing substance is pulverized to have such a particle size, the particles of the calcium component-containing substance are heat-treated uniformly in a short period of time over the range from the surface thereof to the inside in the heat treatment step S3 as described later on. If the calcium component-containing substance is pulverized to be smaller than 100 $\mu$m, it is difficult to handle the calcium component-containing substance since the water in clamshell is not removed yet at this stage and the particles adhere to the inner wall of the heat treatment apparatus. The calcium component-containing substance pulverized to be larger than 20 mm needs a long period of time to heat-treat uniformly in the heat treatment step S3.

Subsequently, in the heat treatment step S3, the calcium component-containing substance is heat-treated. The calcium component-containing substance that is heat-treated expresses the antiviral ability.

The temperature and the time of the heat treatment in the heat treatment step S3 are not necessarily determined in a definite manner since they depend on the type of the calcium component-containing substance to be used as the raw material. However, to obtain a sufficient antiviral ability, the preferable temperature is not less than 650° C. and less than the melting point of the calcium component-containing substance, and the preferable heat treatment time is 2 to 13 hours. If the temperature is less than 650° C. or if the heat treatment time is less than 2 hours, the sufficient antiviral ability is not expressed. The heat treatment melts the ingredient substance containing the calcium component at a temperature of not less than the melting point. Therefore, the ingredient substance containing the calcium component adheres to the inner wall or the like of the heating furnace when it is cooled. Further, to saturate the antiviral ability to be substantially constant, the sufficient heat treatment time is 13 hours. Therefore, the heat treatment that is over 13 hours does not improve the antiviral ability and is not economic. The preferable temperature of the heat treatment is 700 to 1200° C., and the preferable time thereof is 3 to 8 hours.

Finally, in the pulverizing step S4, the heat-treated calcium component-containing substance is pulverized so as to obtain the antiviral agent until the average particle size thereof is not more than 10 μm, preferably not more than 5 μm. The pulverization to obtain fine particles necessarily increases the total surface area of the antiviral agent. In other words, the contact area between the antiviral agent and the virus is increased. Therefore, it is possible to obtain a more excellent antiviral effect.

The pulverizing step S4 is preferably performed after the heat treatment step S3. The pulverizing step S4 performed before the heat treatment step S3 makes it difficult to handle the calcium component-containing substance since the calcium component-containing substance pulverized into the fine particles adheres to the inner wall of the heat treatment apparatus. Furthermore, it becomes difficult to make the average particle size of the antiviral agent to be not more than 10 μm since the particles are partially sintered with each other in the heat treatment S3.

The antiviral agent thus produced is able to be antiviral against coxsackie virus group B type 1, adenovirus type 3, herpes simplex virus type 1, influenza virus type A or the like which are representative viruses in classification. In other words, the infectivity titer of these viruses is greatly decreased and the effect of decreasing the infectivity titer thereof continues for a long period of time.

EXAMPLE 1 AND COMPARATIVE EXAMPLE 1

Oyster shell, for which two years had passed after removing the living body and the adductor muscle had been decomposed and spontaneously separated therefrom, was pulverized to have an average particle size of 10 mm. Subsequently, the pulverized oyster shell was heat-treated in a heating furnace at 850° C. for 7 hours. Further, the oyster shell was finely pulverized to have an average particle size of 10 μm so as to obtain an antiviral agent.

The antiviral agent was mixed with sterilized purified water so that the ratio of the antiviral agent was 0.5% by weight to provide a test sample. Subsequently, 1 ml of a virus solution of a standard strain of coxsackie virus group B type 1 in a solvent of sterilized purified water was mixed with 9 ml of the test sample to effect a reaction for 5 minutes, 15 minutes, 30 minutes, or 1 hour at the room temperature, and then the mixture solution was filtrated with a sterilized filter having a filter size of 0.2 μm. The filtrate was diluted with Eagle's minimum essential medium (hereinafter referred to as "EMEM") at various concentrations to provide test solutions.

On the other hand, 100 μl of cell suspension of cells originating from Rhesus monkey kidney (hereinafter referred to as "MA104 cells"), for which the number of cells was adjusted to be $3.0\times10^5$/ml, was added dropwise to respective wells of 96-well microplate. Next, the MA104 cells were cultured for 3 days under a condition in which the $CO_2$ concentration was 5% and the temperature was 37° C.

The culture medium in the 96-well microplate was exchanged with EMEM added with 5% fetal bovine serum, and 25 μl of respective test solutions was added dropwise to the MA104 cells. Next, the MA104 cells were cultivated at 35° C. for 7 days to determine the 50% cultured cell infectivity titer (hereinafter referred to as "$TCID_{50}$") at respective reaction times. Shown in FIG. 2 are the results indicating that the smaller a value of the infectivity titer is, the smaller the number of infectible viruses is.

For the purpose of comparison, $TCID_{50}$ was determined in accordance with the above procedure except for the use of a solution obtained immediately after mixing 10 ml of a virus solution of a standard strain of coxsackie virus group B type 1 in a solvent of sterilized purified water or after being left to stand still for 1 hour at the room temperature. Results are also shown in FIG. 2.

FIG. 2 makes it clear that, when the coxsackie virus group B type 1 contacts with the antiviral agent according to the embodiment of the present invention, $TCID_{50}$ is greatly decreased even if the contact time is only 5 minutes. In addition, FIG. 2 clearly shows that the longer the contact time is, the more $TCID_{50}$ is decreased.

EXAMPLE 2 AND COMPARATIVE EXAMPLE 2

An antiviral agent was obtained in accordance with a procedure equivalent to that adopted in Example 1. $TCID_{50}$ was determined at respective reaction times in the same manner as in Example 1 except that 1 ml of a virus solution of a standard strain of herpes simplex virus type 1 in a solvent of sterilized purified water was mixed with 9 ml of a test sample obtained by mixing the antiviral agent with sterilized purified water so that a ratio of the antiviral agent could be 0.5% by weight. Results are shown in FIG. 2.

For the purpose of comparison, $TCID_{50}$ was determined in accordance with the above procedure except for the use of a solution obtained immediately after mixing 10 ml of a virus solution of a standard strain of herpes simplex virus type 1 in a solvent of sterilized purified water or after being left to stand still for 1 hour at the room temperature. Results are shown in FIG. 2.

FIG. 2 makes it clear that, when the herpes simplex virus type 1 contacts with the antiviral agent according to the embodiment of the present invention, $TCID_{50}$ is greatly decreased even if the contact time is only 5 minutes.

EXAMPLE 3 AND COMPARATIVE EXAMPLE 3

An antiviral agent was obtained in accordance with a procedure equivalent to that adopted in Example 1. The antiviral agent was mixed with sterilized purified water so that the ratio of the antiviral agent could be 0.5% by weight to provide a test sample. Subsequently, 1 ml of a virus solution of a standard strain of influenza virus type A in a solvent of sterilized purified water was mixed with 9 ml of the test sample to effect a reaction for 5 minutes, 15 minutes, 30 minutes, or 1 hour at the room temperature, and then the mixture solution was filtrated with a sterilized filter having a filter size of 0.2 μm. The filtrate was diluted with minimum essential medium (hereinafter referred to as "MEM") at various concentrations to provide test solutions.

On the other hand, cells originating from dog kidney (hereinafter referred to as "MDCK cells") were washed with phosphate-buffered saline solution. Next, the number of cells was adjusted to be $1.5 \times 10^5$/ml, and 100 μl of cell suspension was added dropwise to respective wells of 96-well microplate and the MDCK cells were cultured for 3 days under a condition in which the $CO_2$ concentration was 5% and the temperature was 37° C.

The respective test solutions were added dropwise to the MDCK cells and were left to stand still under a condition in which the $CO_2$ concentration was −5% and the temperature was 33° C. to enable the MDCK cells to absorb the respective test solutions. Next, $TCID_{50}$ was determined after 100 μl of MEM added with 0.2% bovine serum albumin was added to the MDCK cells and the MDCK cells were cultured at 35° C. for 7 days. Results are shown in FIG. 2.

For the purpose of comparison, $TCID_{50}$ was determined in accordance with the above procedure except for the use of a solution obtained immediately after mixing 10 ml of a virus solution of a standard strain of influenza virus type A in a solvent of sterilized purified water or after being left to stand still for 1 hour at the room temperature. Results are also shown in FIG. 2.

FIG. 2 makes it clear that, when the influenza virus type A contacts with the antiviral agent according to the embodiment of the present invention, $TCID_{50}$ is greatly decreased even if the contact time is only 5 minutes.

EXAMPLE 4 AND COMPARATIVE EXAMPLE 4

An antiviral agent was obtained in accordance with a procedure equivalent to that adopted in Example 1. The antiviral agent was mixed with sterilized purified water so that the ratio of the antiviral agent could be 0.5% by weight to provide a test sample. Subsequently, 1 ml of a virus solution of a standard strain of adenovirus type 3 in a solvent of sterilized purified water was mixed with 9 ml of the test sample to effect a reaction for 5 minutes, 15 minutes, 30 minutes, or 1 hour at the room temperature, and then the mixture solution was filtrated with a sterilized filter having a filter size of 0.2 μm. The filtrate was diluted with EMEM at various concentrations to provide test solutions.

On the other hand, 100 μl of cell suspension of cells originating from human laryngeal cancer (hereinafter referred to as "HEp-2 cells"), for which the number of cells was adjusted to be $1.5 \times 10^5$/ml, was added dropwise to respective wells of 96-well microplate.

$TCID_{50}$ was determined after an amount of 25 μl of the respective test solutions was added dropwise to the respective preparations of the HEp-2 cells and the HEp-2 cells were cultured at 35° C. for 7 days. Results are shown in FIG. 2.

For the purpose of comparison, $TCID_{50}$ was determined in accordance with the above procedure except for the use of a solution obtained immediately after mixing 10 ml of a virus solution of a standard strain of adenovirus type 3 in a solvent of sterilized purified water or after being left to stand still for 1 hour at the room temperature. Results are also shown in FIG. 2.

FIG. 2 makes it clear that, when the adenovirus type 3 contacts with the antiviral agent according to the embodiment of the present invention, $TCID_{50}$ is greatly decreased even if the contact time is only 5 minutes.

In the above Examples 1 to 4, the MA104 cells, the MDCK cells and the HEp-2 cells did not change. Accordingly, it is understandable that the antiviral agent according to the embodiment of the present invention does not damage the health of the animal cells.

As explained above, the antiviral agent of the present invention can decrease the number of viruses such as coxsackie virus group B type 1, herpes simplex virus type 1, adenovirus type 3, influenza virus type A or the like which are representative viruses in classification without damaging the health of the animals and the plants. Accordingly, there is a possibility that the number of SRSV can be also decreased.

The antiviral agent of the present invention uses the heat-treated calcium-containing substance as the active ingredient. Therefore, the liberated chlorine and the methane trihalide, which are regarded to be unfavorable for the health of animals and plants, do not adhere to the food material, unlike the aqueous sodium hypochlorite solution.

The method of producing the antiviral agent of the present invention makes it possible to obtain the antiviral agent of the excellent antiviral ability highly efficiently. Therefore, even if an amount of consuming or distributing food materials is increased, it is possible to stably supply a large amount of the antiviral agent.

What is claimed is:

1. An antiviral agent consisting essentially of an effective amount of an active ingredient prepared by:

(1) washing a calcium component containing substance selected from the group consisting of clamshell, eggshell, crustacean shell, coral and pearl;

(2) performing a pre-pulverizing step by pulverizing said calcium component containing substance into a granular form so that an average particle size is 100 μm to 20 mm;

(3) heat-treating the calcium component containing substance from step (2) at a temperature of from 700° C. to 1200° C. for 3 to 8 hours;

(4) cooling the heat-treated calcium component containing substance from step (3); and (5) pulverizing the cooled calcium component containing substance from step (4) to obtain an active antiviral ingredient with an average particle that is between 5 μm and 10 μm.

2. The antiviral agent according to claim 1, wherein said antiviral agent has an antiviral ability against adenovirus type 3, herpes simplex virus type 1, coxsackie virus group B type 1, and influenza virus type A.

3. The antiviral agent according to claim 1, wherein said clamshell is oyster shell.

4. The antiviral agent according to claim 3, wherein said antiviral agent has an antiviral ability against adenovirus type 3, herpes simplex virus type 1, coxsackie virus group B type 1, and influenza virus type A.

5. A method of producing an antiviral agent comprising:

(1) washing a calcium component containing substance selected from the group consisting of clamshell, eggshell, crustacean shell, coral and pearl;

(2) performing a pre-pulverizing step by pulverizing said calcium component containing substance into a granular form so that an average particle size is 100 μm to 20 mm;

(3) heat-treating the calcium component containing substance from step (2) at a temperature of from 700 C. to 1200° C. for 3 to 8 hours;

(4) cooling the heat-treated calcium component containing substance from step (3); and (5) pulverizing the cooled calcium component containing substance from step (4) to obtain an active antiviral ingredient with an average particle that is between 5 $\mu$m and 10 $\mu$m.

6. The method of producing said antiviral agent according to claim 5, wherein shell, which has been left to stand for not less than two years after removing a living body of clam therefrom, is used as said calcium carbonate-containing substance originating from said animal.

7. A method of producing an antiviral agent comprising:

(1) providing a calcium containing substance, which is clamshell that has been left to stand for not less than two years after removing a living body of claim therefrom, (2) performing a pre-pulverizing step by pulverizing said calcium component containing substance into a granular form so that an average particle size is 100 $\mu$m to 20 mm;

(3) heat-treating the calcium component containing substance from step (2) at a temperature of from 700° C. to 1200° C. for 3 to 8 hours;

(4) cooling the heat-treated calcium component containing substance from step (3); and (5) pulverizing the cooled calcium component containing substance from step (4) to obtain an active antiviral ingredient with an average particle that is between 5 $\mu$m and 10 $\mu$m.

* * * * *